United States Patent
Ott et al.

[11] Patent Number: 6,045,511
[45] Date of Patent: Apr. 4, 2000

[54] DEVICE AND EVALUATION PROCEDURE FOR THE DEPTH-SELECTIVE, NONINVASIVE DETECTION OF THE BLOOD FLOW AND/OR INTRA AND/OR EXTRA-CORPOREALLY FLOWING LIQUIDS IN BIOLOGICAL TISSUE

[75] Inventors: Lutz Ott, Fernwald; Rudolf Steiner, Ulm; Paul Jurgen Hulser, Kisslegg, all of Germany

[73] Assignee: Dipl-Ing. Lutz Ott, Germany

[21] Appl. No.: 08/845,216

[22] Filed: Apr. 21, 1997

[51] Int. Cl.[7] .......................................................... A61B 5/02
[52] U.S. Cl. .......................... 600/504; 600/473; 600/476
[58] Field of Search ................................ 600/310, 322, 600/473, 476, 481, 504; 356/27, 28, 39; 250/559.32

[56] References Cited

U.S. PATENT DOCUMENTS

| | | | |
|---|---|---|---|
| 4,154,529 | 5/1979 | Dyott | 356/28 |
| 4,476,875 | 10/1984 | Nilsson et al. | 600/504 |
| 5,490,523 | 2/1996 | Issacson et al. | 600/322 |
| 5,529,065 | 6/1996 | Tsuchiya | 600/310 |
| 5,598,841 | 2/1997 | Taniji et al. | 600/504 |

*Primary Examiner*—Linda C. M. Dvorak
*Assistant Examiner*—Bryan K. Yarnell
*Attorney, Agent, or Firm*—Liniak, Berenato, Longacre & White

[57] ABSTRACT

A device and an evaluation procedure for the depth-selective, non-invasive detection of the blood flow and/or intra- and/or extracorporeally flowing liquids in biological tissue are described whereby photons of a coherent, monochromatic source of light are entered into the tissue through a first area, photons reemerging from the tissue at different distances from this first area are detected with respect to their frequency and number, or intensity, and, from this information, i.e. frequency and/or number, or intensity, and/or reemerging location, conclusions about the relative modification of the flow amount and/or speed and/or location of the blood flow and/or the intra- and/or extracorporeally flowing liquids in the tissue are drawn with the help of an evaluation program or algorithm.

20 Claims, 4 Drawing Sheets

DEVICE AND EVALUATION PROCEDURE FOR THE DEPTH-SELECTIVE, NONINVASIVE DETECTION OF THE BLOOD FLOW AND/OR INTRA AND/OR EXTRA-CORPOREALLY FLOWING LIQUIDS IN BIOLOGICAL TISSUE

BACKGROUND OF THE INVENTION a) Field of the Invention

The invention refers to a device as well as to an evaluation procedure for the depth-selective, non-invasive detection of the blood flow and/or intra- and/or extra-corporeally flowing liquids in biological tissue.

b) Description of Related Art

The skin as a liminal organ between the human being and his environment has multiple functions. It accomplishes regulatory as well as immunological tasks and, last but not least, serves as a sense organ. In rough outlines, the skin is composed of the epidermis and the layer lying beneath it, called the corium, which consists of nerves, muscles and capillaries. The regulation of the microcirculation and the control of all other functions of the skin is realized through the interplay of these muscles, nerves and capillaries. A determination and control of the perfusion of the skin can now serve to detect perfusive variations and disturbances and to support a medical diagnosis. In the following a selection of the manifold applications is listed in catchwords:

Diagnosis of dermatological diseases, e.g. scleroderma, psoriasis

Localization of manifestations of arteriosclerosis

Assistance with the identification of cases of diabetic microangiopathy

Observation of the arterial vasomotion

Control of the functions of the sympathicus in the field of local anaesthesia

Perfusion control with respect to transplantations, etc.

Laser Doppler systems have been used for decades for the diagnostic process in the field of dermal vessels. The most important restrictions of the conventional laser Doppler systems are their limited effective invasion depth and the analysis of isotropic signals. Thus, their use is limited to the measuring of the microcirculation of the skin, in the course of which a measuring volume of the size of a hemisphere with a maximum diameter of 1 mm may be analyzed. Furthermore, the devices for the investigation of the perfusion of the skin that have been used clinically up to now do not supply comparable measuring values. The users of these conventional systems, e.g. Flowmeter, have passed on to refer to the temporal reaction of the measuring values according to determined stimulations for the evaluation of the microcirculation.

SUMMARY OF THE INVENTION

Therefore the task of the invention is to develop a device as well as a procedure for the non-invasive, depth-selective detection of the blood flow and/or intra- and/or extracorporeally flowing liquids in biological tissue.

With respect to the device, this task is resolved essentially in this way that a coherent, monochromatic source of light, in particular a laser, for the emission of photons into the tissue, through a locally well-defined first area of skin that possibly covers the tissue, is planned, and that the device consists of several detectors for the registration of the photons reemerging from further superficial areas of the skin or of the tissue, whereby the further superficial areas are located in different distances from the first area.

The novel evaluation procedure is characterized essentially by the feature that photons of a coherent, monochromatic source of light are entered into the tissue of a first area, and that photons reemerging in different distances from this first area are detected with respect to their frequency and number, or intensity, and that, with the help of an evaluation program and/or evaluation algorithm, conclusions about the relative modification of the flow amount and/or speed and/or location of the blood flow and/or other intra- and/or extra-corporeally flowing liquids in the tissue are drawn from this information, i.e. frequency and/or number and/or intensity and/or emerging location of the reemerging photons.

This device or this evaluation procedure, respectively, make use of the characteristic of interaction between electromagnetic waves and tissue and components of blood and/or liquids. Due to an adequately small wave length and to the ensuing sufficient ratio between the wave length and the geometrical dimension of the body or tissue to be detected, the spectral range of visible to infrared electromagnetic waves is suitable. Simultaneously, a sufficient detection depth into the biological tissue is reached. This procedure is non-invasive and the modifications resulting from the interaction are proportional to the speed, the number and the depth of the individual flowing components of blood and/or liquids. Consequently, a relative modification of the flow amount or the like is unmistakably provable and assignable with this information in particular. Examinations in everyday clinical practice as well as with respect to special medical, pharmacological and industrial problems with regard to the depth-selective detection of the blood flow and/or intra and/or extracorporeally flowing liquids may be executed very easily, without pain and reproducibly with this device or evaluation procedure, respectively.

The invention is based on the fact that coherent and monochromatic rays are radiated onto the surface of the skin or of the tissue of the areas to be detected with the help of laser light or the like. The photons invade into the tissue and are scattered or absorbed, respectively, in accordance with the optical parameters of the tissue. Since the scattering is accompanied by a modification of the scattering direction of the photons, photons are also remitted from the tissue, i.e., they are re-scattered to the surface of the tissue or the skin, respectively, and reemerge from the tissue. This re-emission of the photons reemerging from the tissue is characterized by a decreasing intensity the longer the distance from the entering location of the photons is. Another feature of the biological tissue is that the light is not scattered evenly, i.e. isotropically, into all directions, but that a forward motion is maintained during the scattering process. This is expressed in the so-called anisotropy factor 'g' for scattering which suggests a value 'g' of 0.9 for tissue. A value g=O would stand for isotropic scattering whereas a value g=1 stands for direct forward scattering.

In the following it is to be explained on the basis of a simple model how a conclusion about the status of the tissue or the blood flow and/or the intra- and/or extracorporeally flowing liquids may be drawn via the detection of remitted photons. When photons are examined that, e.g., reemerge from the tissue 5 mm beside the radiation location it is very likely that these reemerging photons have moved along an approximately semicircularly or similarly curved track through the tissue due to several scattering processes. In virtue of the special array of the measuring device or of the execution of the evaluation procedure, respectively, it is certain, however, that the beginning of the curved track is the entering location of the photons and the end of the track is the measuring point of the reemerging photons. Provided that these reemerging photons carry any information with respect to the motion of the blood flow and/or the intra- and/or extracorporeally flowing liquids at all, it may be assumed that the photons reemerging immediately beside the radiation location carry only information with respect to layers of tissue flown through closely below the surface, whereas photons reemerging at longer distances from the radiation location may also give information about deeper layers flown through. This model view makes it clear that, with the help of a detection of photons reemerging from the tissue, selective information may be gathered from determined tissue depths the longer the distance from the radiation location is.

As it is generally known, the optical Doppler effect is used in order to measure moving, scattering particles. During the scattering process, the light undergoes a frequency shift which increases proportionally to the speed of the moved particle. Taking into account the Doppler effect, thus the blood flow in tissue may be determined, e.g. in superficial layers of tissue. A light wave length of the source of light, in particular of the laser, that is absorbed by the tissue only slightly is necessary in order to achieve an optimal Doppler signal of the blood flow and/or the intra- and/or extracorporeally flowing liquids in deeper layers of the tissue. Therefore, wave lengths in the range between 600 nm up to 1200 nm are suitable, the preferred wave length is about 820 nm.

In the technical literature there is discussion from time to time that coherent laser light might lose its characteristics of coherence by the multitude of scattering processes when it is radiated into the tissue, However, it may be demonstrated by interferometric tests that a certain percentage of the photons that emerge at a longer distance from the radiation location from the tissue may interfere with the incident ray of photons which leads undoubtedly to the conclusion that the characteristics of coherence of these scattered photons still exist. Thus, it is possible to detect Doppler signals with the respective frequency shift of the reemerging photons even at longer distances from the radiation location. In this process, photons with Doppler shifted frequency mingle with such photons that did not undergo a frequency shift, i.e., that were scattered by a rigid or motionless matrix. This way, an intensity beat between frequency shifted and non-frequency shifted photons occurs at the detection location on the surface of the tissue. This leads to a local speckle pattern the intensity of which varies with the Doppler frequency and may thus be measured with an optical detector.

The evaluation of the signals is conducted in principle in this way that two detectors, preferentially arranged symmetrically to the radiation location, register the reemerging photons. The output signals of these detectors are evaluated and processed adequately in order to gather the desired information or statements with respect to the blood flow and/or the intra- and/or extracorporeally flowing liquids.

It may be said that an evaluation process of the present invention is especially usable in the field of the therapeutical window, i.e., at wave lengths in the range between 600 nm and 1200 nm, where the scattering of the radiated photons is not negligible. The optical absorption from the scattering of light in human tissue may be described more precisely with the help of the photon transportation theory. Hereby, the path of a photon scattered into the skin is observed. The photon undergoes either an elastic scattering or it is absorbed completely at the individual local dispersers. The invasion depth and the scattering process may thus be determined for the laser light of the red wave length range (600 nm) and of the infrared wave length range (1200 nm), respectively. Although the so-called average free path length is relatively short, light of this wave length range may invade deeply into the tissue, since the scattering mainly follows the forward direction (so-called Mie scattering), the scattering processes are essentially more frequent than the absorption processes and the absorption in the tissue in this wave length range is low compared to other wave lengths. The dissemination of light in the tissue is described in the transportation theory by the following parameters: anisotropy factor, scattering coefficient, absorption coefficient, average free path length.

An overall view of the conducted theoretical as well as experimental investigations suggests that annular interference structures grouped concentrically with respect to the radiation location become available with the present procedure or device, respectively. With an increasing lateral distance from the point of radiation, it is very likely that the photons cover longer distances in the tissue and invade adequately deeper into the tissue. In order to evaluate the information about the motions of the lighted tissue contained in the photon status, the source of light ought to have specific characteristics, el g., have a sufficient coherence length, be monochromatic and be operable in the single-mode status.

An important precondition for obtaining the desired information is a sufficiently high coherence length in order to achieve an interference pattern on the surface of the present device. The formation of the interference pattern bases on the assumption that photons which are scattered near to the surface of the tissue or of the skin do not undergo any frequency modifications whereby the photons that in a way are not scattered interfere with those photons that are scattered at moving components of the blood and/or of liquids in the depth and thus undergo a frequency modification. When the frequency shifted scattered light which was scattered at moving particles is made coincident on the surface of the detector with the non-frequency shifted, in a way original, light a beat frequency or an interference pattern is developed. The use of a wave length in the range between 600 nm up to about 1200 nm is necessary in order to achieve these beat frequencies from deeper layers of tissue. At the same time, a sufficient coherence length of the source of light is to be taken into account. It was demonstrated that typical interference patterns are even provable for far depths and that the information originates from increasing depths of the tissue the longer the distance from the detector surface is. This was also shown successfully for long lateral distances of the detector surface from the radiation location in a range of up to 15 mm. Even lateral distances of up to 30 mm seem to be basically possible in practice.

The present device is characterized by a number of advantageous configurations.

According to a first advantageous version of the present device, it is for example possible that there is at least one optical fibre guide to be placed or attached on the front side of the tissue or a collimation optic to focus the laser light on the tissue or on the skin that is tandem-arranged with the source of light. This way, a locally defined radiation of the photons into the tissue is guaranteed. The optical fibre guide preferentially ought to be a multimode or monomode fibre with a diameter of about 50 nm to 450 nm or more in order to be able to transmit the light efficiency of the semiconductor laser. However, multi-mode fibers may also be used. Depending on the version, it is possible to do without an optical fibre guide, e.g., if the laser light is focussed onto the surface of the skin with a collimation optic.

Furthermore it has proved to be very advantageous that the detectors are equipped in any case with an optical fibre that may be placed or attached on the front side of the tissue and assigned to it, there is a photodiode or the like. Thus, the surface of the detector consists of optical fibre guides polished at their front sides the spatial distribution of the light current of which is organized in a way that the received light is in any case transmitted to the sensitive surface of a photodiode.

The use of a polarization filter assigned to the source of light or installed before the detectors has proved to be suitable for the improvement of the signal quality, whereby an additional absorption filter may be assigned to the detectors. These filters may be vapor-deposited or may have the form of a separate glass insert.

The advantageous wave lengths of the source of light, preferentially a semiconductor laser, lie in the range between 600 nm up to about 1200 nm, whereas the preferred wavelength is about 820 nm. This wave length range is also called the "therapeutic window".

The provision that the further superficial areas or the assigned detectors are arranged neighboring in pairs and essentially are connected in series whereby each pair has got another distance from the first area and that the distances of neighboring pairs are in particular equidistant proves to be an especially advantageous, independent design of the invention. Thus, in each case, two detector surfaces are planned that are arranged in pairs side by side and symmetrically to the radiation location of the photons at a defined distance from it. Each of the superficial areas in pairs or detectors, respectively, thus represents a measuring volume of the tissue to be analyzed. Each of the detectors in pairs ought to receive an equivalent signal due to the distribution of the light in the tissue.

According to another version of the invention, there is also the possibility that the further superficial areas or the assigned detectors are arranged along a straight line leading through the first area and in pairs symmetrically on both sides of the first area. Presuming a preferential direction of the light dissemination in the tissue, the problem may arise with this version, however, that the detectors or superficial areas, respectively, register different Doppler frequencies of the reemerging photons and a wrong measuring result is thus provided.

Basically, it is of course also possible to use only one single further superficial area or detector per detection channel, The registration of measuring values, however, proves to be extremely more difficult in this case due to the more unfavorable signal-noise-ratio.

As the practical investigations have shown, the further superficial areas or the corresponding detectors for the registration of the photons reemerging from the tissue are arranged up to a maximum distance of about 15 to 30 mm from the first area. This maximum distance is in essence dependent on the wave length used and on the absorption coefficient linked to it as well as on the coherence length of the source of light used.

With respect to the evaluation of the detector signals, it has proved to be especially advantageous that the two signals registered by the superficial areas in pairs or the corresponding detectors are both conducted to the two inputs of a differential amplifier. The use of a differential amplifier is advantageous in the way that the static portion of the signal of the detectors connected in pairs is compensated due to the amplification of the input voltage difference applied at the inputs only and that thus, only the dynamic intensity fluctuations which are determined by the optical Doppler effect and this way by the moved components of the blood and/or the liquids are amplified. This provision leads to an enormous improvement of the signal-noise-ratio and thus to a considerably more precise evaluation of the signals since only the intensity fluctuations due to the motions of the tissue are amplified.

Since the signals of the detectors, possibly after a digitalization, are submitted to an adaptive filter function as well as to a cepstrum analysis function the useful signal remains unaffected due to the filtering on one hand, and the characteristic, changing frequency portions of the signals may be made visible on the other hand.

According to another advantageous aspect of the invention, the source of light as well as the detectors and electronic components, e.g. a possible preamplifier, differential amplifier and possibly an analogue-to-digital converter are housed together in a measuring head that may be attached to the tissue or skin flatly whereby the measuring head is connectable to the evaluation unit, in particular to the processor, via electric conductors merely. This measuring head may be for example about 130 mm high and about 15 mm wide and may have rounded lateral faces. However, other housing designs according to individual requirements are also conceivable. The whole device, apart from the processor, is arranged on a single mounting plate or board or the like which is housed in a closed, physiologically harmless and shielded housing made of synthetic materials.

An especially advantageous design of the above explained present evaluation procedure is that a source of light with a high coherence length, in particular higher than 10 cm, is used and that the reemerging photons in any case are detected at a certain distance from the first area, especially simultaneously in at least two superficial areas, closely neighboring or arranged symmetrically to the first area. This provision creates the precondition for a very good signal-noise-ratio.

It has proved to be advantageous in this connection that the detected signals of two superficial areas, respectively, are conducted to a differential amplifier function, among others, as well as that they are submitted to a possible adaptive filter function and possibly to a frequency and/or cepstrum analysis. A precise analysis of the activities of the muscles may be obtained by this kind of procedural signal evaluation.

Further aims, advantages, features and applications of the present invention follow from the ensuing description of the versions illustrated by the figures. Hereby, all described and/or illustrated features by themselves or in any possible efficient combination represent the object of the present invention, even independent from their summary in the claims or from their reference.

DETAILED DESCRIPTION OF THE PREFERRED EMBODIMENT

Figure 1:
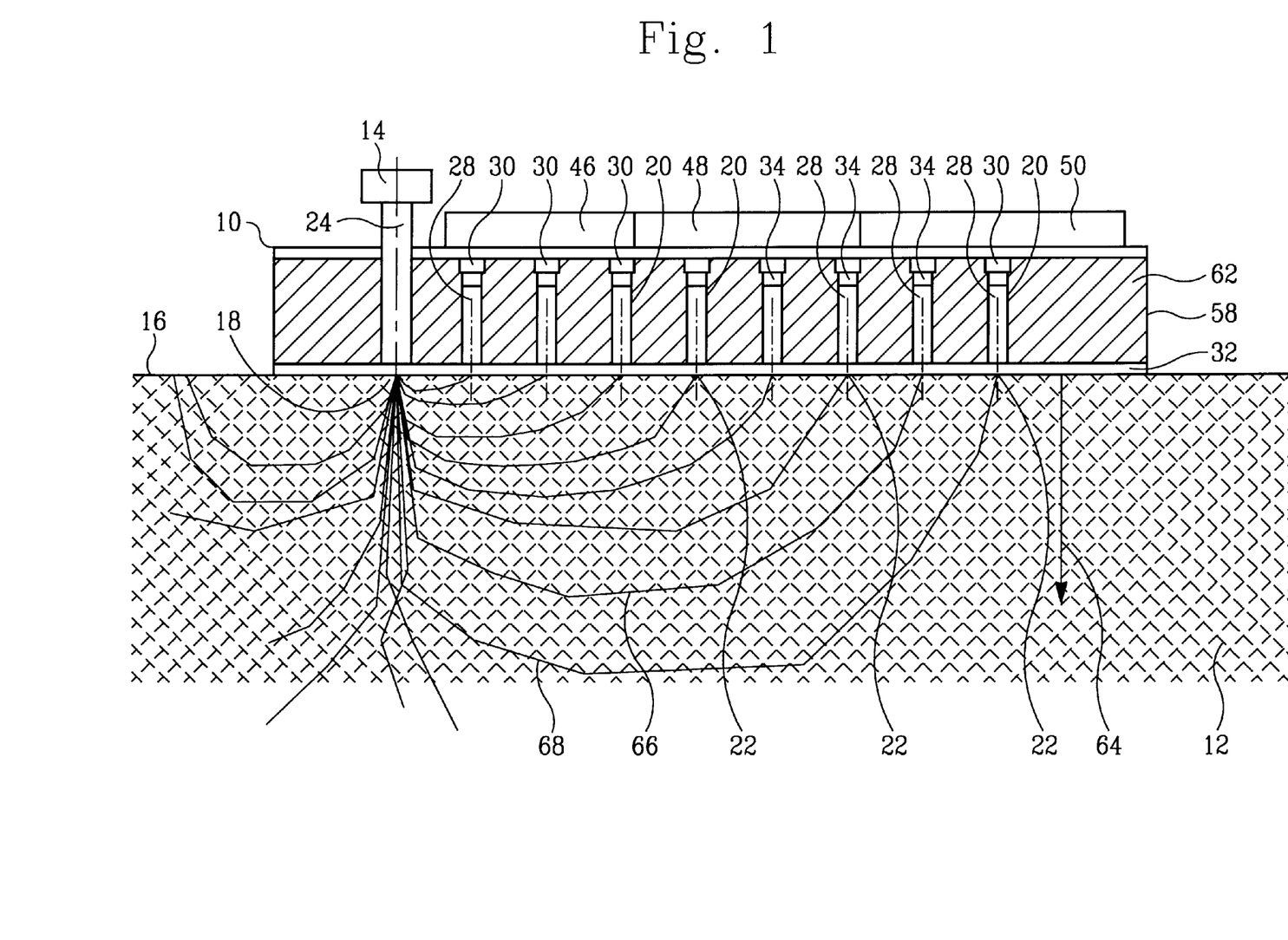
FIG. 1 is a schematic view of a first version of the present device attached to the tissue in a side view.
Figure 2:
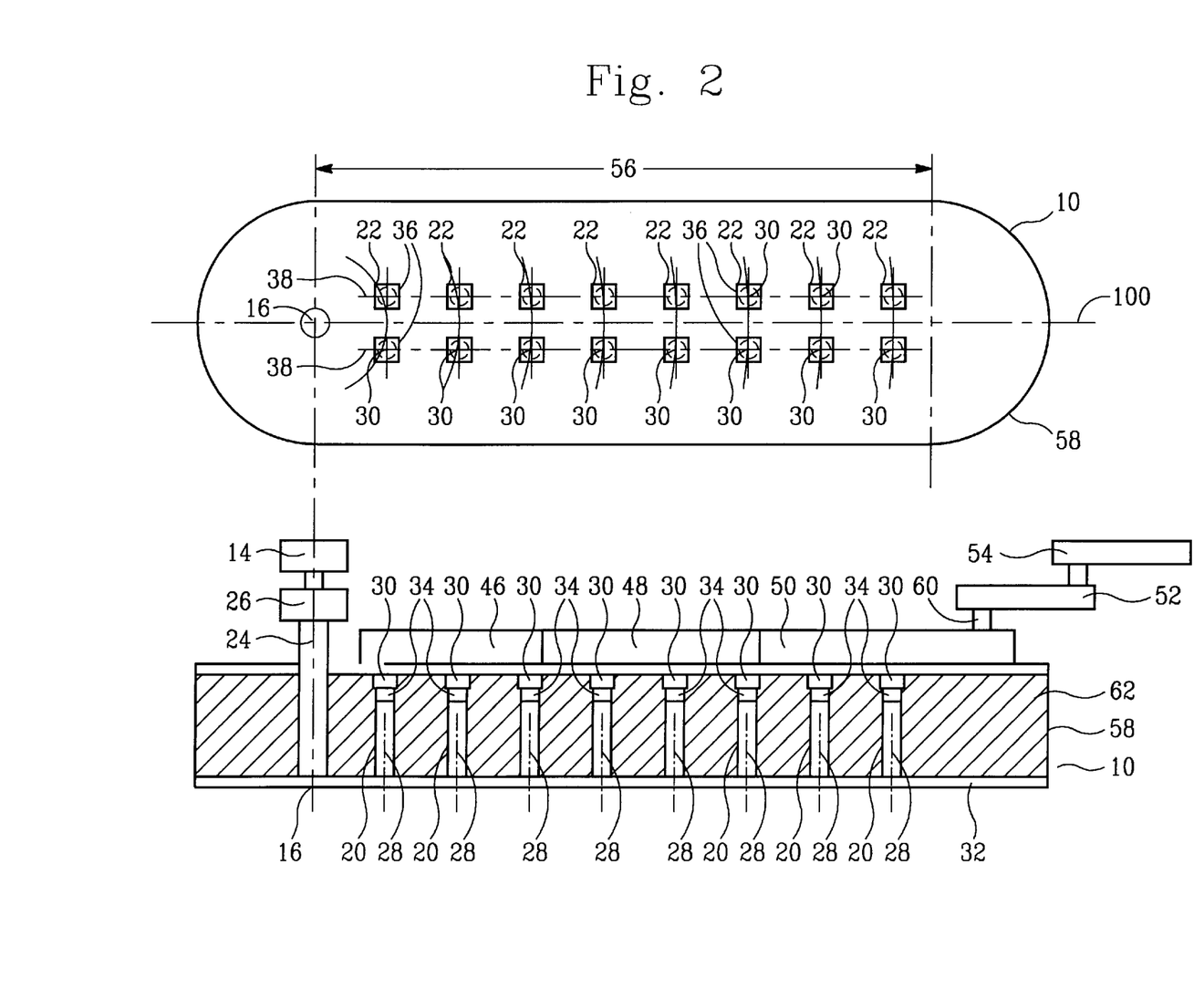
FIG. 2 is a second version of the present device in a side view and an underside view.

The device 10, shown in FIGS. 1 and 2, for the depth-selective detection of the blood flow and/or intra- and/or extracorporeally flowing liquids in human, animal or suchlike tissue 12 features a source of light 14, in particular a semiconductor laser, for the emission of photons into the tissue 12 or into the blood vessels, respectively. The device to is attached to the tissue 12 or to the skin 18 of the tissue with the help of a mounting plate, whereby the photons enter into the tissue 12 or the blood vessels, respectively, through a first area 16 that is, in essence, locally well-defined. In the tissue 12 or in the blood vessels, respectively, the photons are partially scattered and partially absorbed whereby some possible tracks of the photons 66, 68 are represented graphically and schematically in FIG. 1. It is clearly visible that the photons reemerge from the tissue 12 the farther away from the first area 16 the higher the $i_n$nvasion depth 64 is.

Furthermore, the device 10 features several detectors 20 for the registration of the photons reemerging from further superficial areas 22 of the skin 18 or the tissue 12, respectively, The further superficial areas 22 are arranged at different distances from the first area.

An optical fibre guide 24 that is attachable or placeable on the front side of the tissue 12 is assigned to the source of light 14 according to the version in FIG. 1. However, the version in FIG. 2 makes it clear that a collimation optic 26 to focus the laser light on the tissue 12 or the skin 18, respectively, may be used instead of an optical fibre guide 24.

The detectors 20 feature each an optical fibre 28 attachable or placeable on the front side of the tissue 12 to which a photodiode 30 or the like is assigned.

A polarization filter is assigned to the source of light 14 and connected in front of the detectors 20. Furthermore, absorption filters 34 may be installed between the fibre light guide 28 and the photodiode 30.

The wave length of the semiconductor laser lies in the range of about 600 nm up to about 1200 nm, whereas the favorite wave length is about 820 nm.

As it is especially obvious from the version in FIG. 2, the further superficial areas 22 or the assigned detectors 20, respectively, are arranged neighboring in pairs and essentially in series 38, whereby each pair 36 has got another distance from the first area 16 and the distances of neighboring pairs 36 are at least in this version equidistant. It goes without saying that other distances of the individual detectors 20 with respect to the first area 16 may be chosen. This is assessed by the special requirements of the system in question and the technical knowledge of the average expert. The further superficial areas 22 or the corresponding detectors 20, respectively, are arranged up to a maximum distance 56 of about 15 to 30 mm away from the first area 16.

Figure 3:
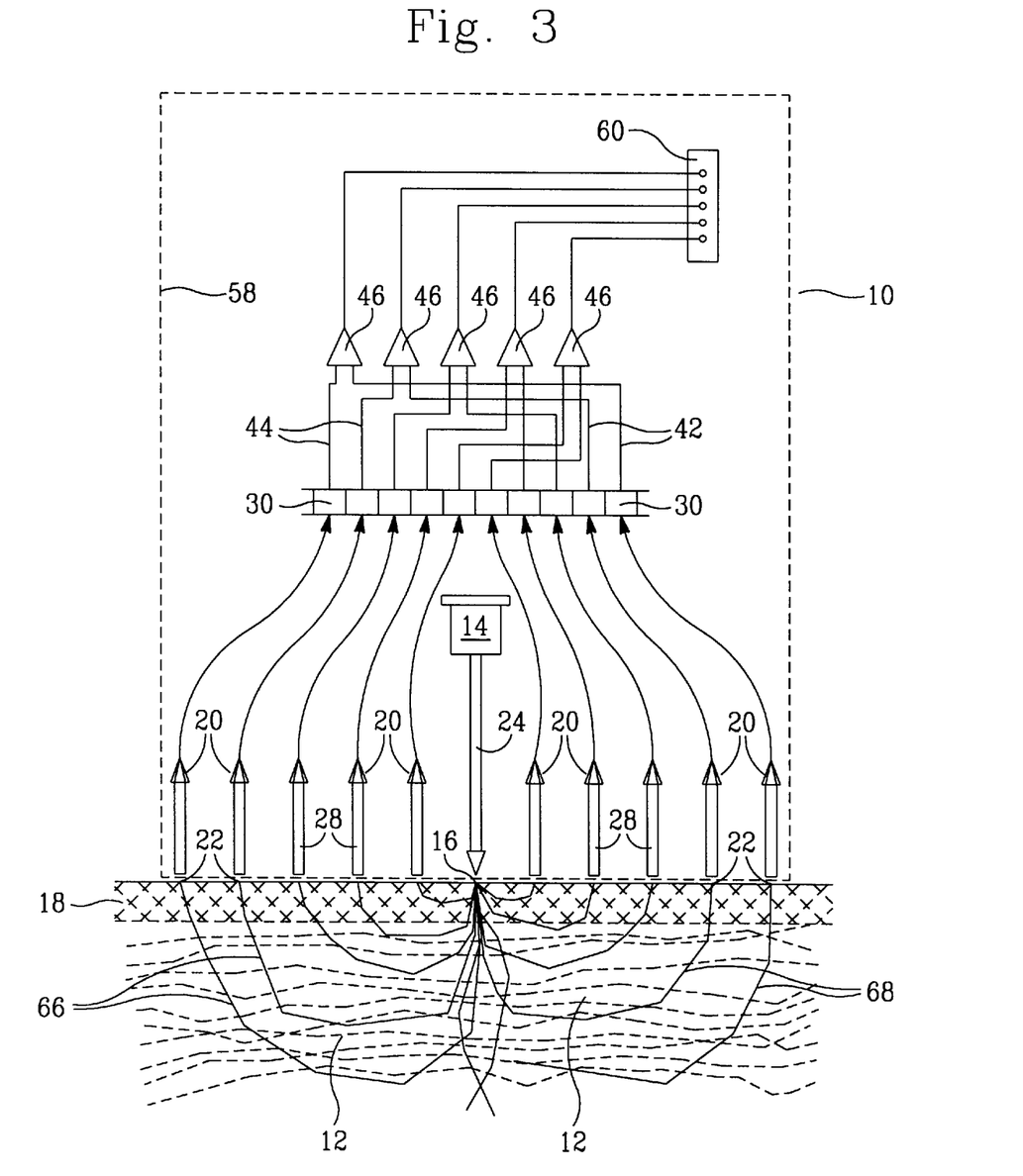
FIG. 3 is a third version of the present device in a schematic drawing.

As it becomes especially clear from FIG. 3, the two signals 42, 44 that are registered by the superficial areas 22 in pairs or by the corresponding detectors 20, respectively, are both conducted to the two inputs of a differential amplifier 46. This provision is advantageously applied with the versions in FIGS. 1 and 2, too, whereby in these cases corresponding pairs 36 of detectors 20 are connected to a differential amplifier 46. The signals of the detectors 20 are, among others, submitted to an adaptive filter function 52 as well as to a cepstrum analysis function 78 (see FIG. 5).

The whole device, apart from a processor 54, i.e., the source of light 14, the detectors 20 and the electronic components, as possibly preamplifiers 48, differential amplifiers 46 as well as analog-to-digital converters 50, is housed together in a measuring head 58 that is attachable flatly onto the tissue 12 or the skin 18, respectively. Thus, the measuring head 58 features one mere connection via electrical conductors to the evaluation unit, in particular to the processor 54. The interior of the measuring head is filled with a filler 62.

Varying from the array of the detectors 20 in the versions of FIGS. 1 and 2, the version according to FIG. 3 features further superficial areas 22 or assigned detectors 20, respectively, that in essence are arranged along a straight line 40 running through the first area 16 and in pairs, symmetrically on both sides of the first area 16.

Figure 4:
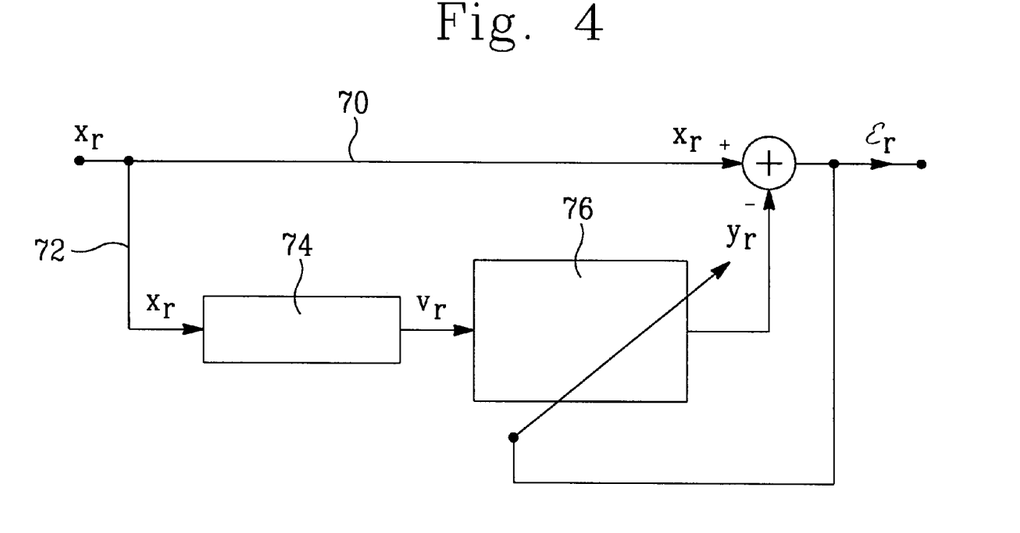
FIG. 4 A block diagram of an adaptive filter function.

The adaptive filter function 52 in FIG. 4 features two channels 70, 72, whereby the first channel 70 conducts the unaffected input signal whereas a deceleration stage 74 is installed in channel 72. The filter coefficients are changed with the help of the adaption stage 76 until the difference between the unfiltered input signal of channel 70 and the filtered signal of channel 72 in the quadratic average becomes minimal.

Figure 5:
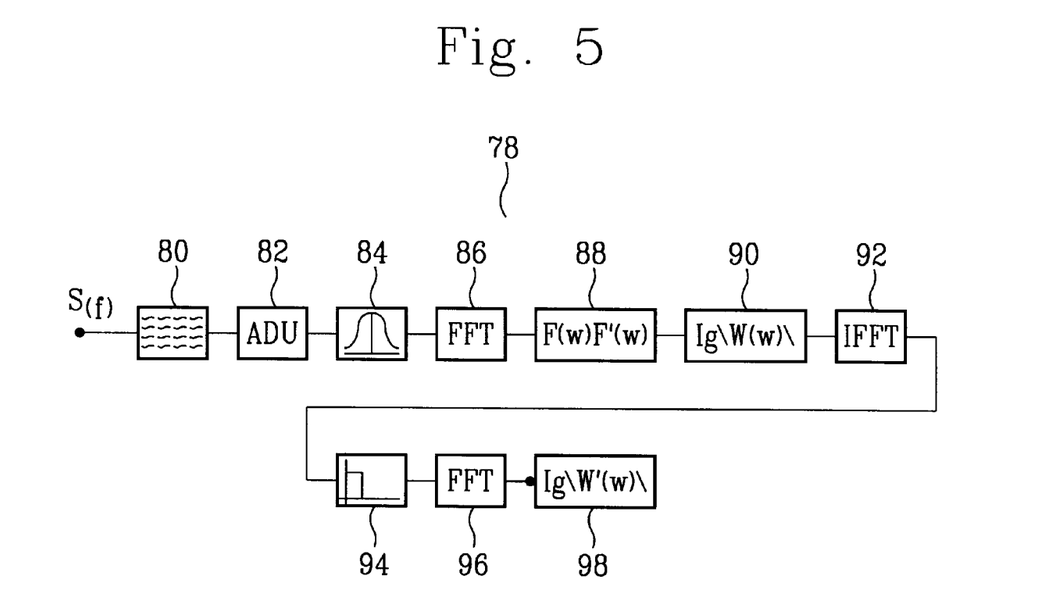
FIG. 5 A block circuit diagram of a cepstrum analysis function.

According to FIG. 5 representing a block circuit diagram of the cepstrum analysis function 78, the signals are displayed graphically in the shape of a time-amplitude-function and dispersed into a performance spectrum 88 or into a power spectrum with a real-value Fast-Hartley Transformation (FHT) or with a Fast-Fourier Transformation (FFT) or with another frequency analysis algorithm. Hereby, the partial frequencies contained in the beat frequency are analyzed with respect to their intensity and bandwidth. The performance spectrum 88 is determined in real-time with a number of points of support bigger than 64 and is represented graphically for each analogue-to-digital converter 82 in a kind of a "waterfall diagram". This performance spectrum is submitted to a moment analysis of the intensity as well as of the frequency. The moments formed in this way may be combined in a vector and be represented graphically. The cepstrum analysis 78 altogether consists of the serial array of a filter function 80, an analogue-to-digital converter 82, a discrete time window 84, a Fast-Fourier Transformation 86, a performance spectrum 88, a logarithmic function 90, an inverse Fast-Fourier Transformation 92, a lifting function 94, a Fast-Fourier Transformation 96 and finally a modified performance spectrum 98. This latter procedure is also called cepstrum analysis function 78 by which characteristic, changing frequencies may be made visible. The significance of the cepstrum analysis function consists especially in the feature that spectra with periodical fluctuations may be submitted to a precise analysis. The cepstrum is derived from the phase-free performance spectrum.

All measuring values, evaluations and analyses may be visualized for the user on a graphical user interface and may be stored in mass memories for further processing. The different signals may furthermore be compared with each other and evaluated by a cross correlation, an autocorrelation or another algorithm for the evaluation of signals.

The version of FIGS. 1 and 2 in essence functions as follows. A semiconductor laser housed in the measuring head 58 radiates coherent, monochromatic light, in particular of a coherence length higher than 10 cm, directly into the optical fibre guide 24. The light is transmitted through the optical fibre guide 24 to the surface of the skin 18 in the first area 16. The optical fibre guide 24 preferentially ought to be a multimode or monomode fibre with a minimum diameter of about 50 nm to 450 nm in order to transmit the performance of light of the semiconductor laser. Depending on the version, it is possible to do without the optical fibre guide 24 if the laser light is focussed immediately on the surface of the skin with the help of a collimation optic 26. The reemerging light is received at the optical fibers 23 in the further superficial areas 22 and transmitted to the photodiodes 30. There are absorption filters 34 or polarization filters 32, respectively, in front of or behind the optical fibers 28 and/or in front of the optical fibre guide 24.

All fibers and filters preferentially are fixed on a lightproof frame made of synthetic material or ceramics on the measuring head 58. The fibers are arranged in pairs, off-center to a longitudinal axis 100 on a mounting plate of the measuring head 53. The distance between the individual pairs 36 is equal whereby this distance may be arranged variably in different versions. The optical fibers 28 have a diameter of about 50 nm to 450 nm, and should not exceed a diameter of 400 μm since the signal-noise-ratio improves the smaller the diameter is. However, the smaller the diameter becomes the lower the intensity of the measuring signal will be. Therefore, a compromise is to be made. When choosing the photodiodes 30, special attention is to be paid to the feature that the individual photocurrents vary only minimally with equal lighting. The complete evaluation electronics, consisting of preamplifier 48 and differential amplifier 46, is integrated in the shielded housing of the measuring head 58. The analogue-to-digital converters 50, too, may be housed in the measuring head 58. There is, however, the opportunity to place these components outside the measuring head 58 on a measuring board in order to transmit only digitalized signals to the processor 54. The task of the evaluation electronics is to convert the current coming from the photodiodes 30 into a voltage and to amplify it. This is realized with the help of the preamplifier 48. Thereafter, a signal difference is created and further amplified by the photodiodes arranged and connected in pairs 30 with the help of the differential amplifiers 46. Eventually, an analogue-to-digital converter 50 with a resolution of 12 to 16 bit and a minimum scanning rate of about 20 kHz is assigned to the differential amplifier 46. Thus, an analogue-to-digital converter is assigned to each pair of the photodiodes. The digitalized signals are transmitted to the processor 54 for evaluation.

It is worth mentioning that, contrary to the version in FIGS. 1 and 2, the pairs 36 of photodiodes 30 or the superficial areas 22, respectively, in the version according to FIG. 3 are not arranged side by side in pairs, but in a way diametrically and symmetrically to the left and the right, respectively, of the first area 16. With this version, too, it is possible to achieve better signal-noise-ratios via a formation of a difference of the output signals of corresponding pairs 36 of photodiodes 30. This array may, however, be somehow disadvantageous, especially if there is a preferential direction of light dissemination in the tissue.

Therefore, the versions represented in FIGS. 1 and 2 concerning the array of the photodiodes 30 or the further superficial areas 22, respectively, in pairs are a preferential version of the invention.

While the present invention has been shown and described with reference to preferred embodiment, it will be understood by those having skill in the art that various changes in form and detail may be made therein without departing from the spirit and scope of the invention.

We claim:

1. A device (10) for a non-invasive detection of one of a blood flow and intracorporeally and extracorporeally flowing liquids in one of a human and animal tissue (12); said device comprising a coherent, monochromatic source of light (14) including a laser, for emission of a plurality of photons into the tissue (12), through a first area (16) of skin (18) covering the tissue (12), at least one detector (20) for registering the photons reemerging from one of a plurality of superficial areas (22) of the skin (18) whereby the plurality of superficial areas (22) are located at different distances from the first area (16); and a detection means for selectively detecting a blood flow a selective depth below said skin.

2. The device according to claim 1, wherein at least one of an optical fiber guide (24) placeable on a front side of the tissue and a collimation optic to focus the laser light on the tissue (12) respectively, is assigned to the source of light (14).

3. The device according to claim 1, wherein each detector (20) comprises an optical fiber (28) attachable on a front side of the tissue (12) to which a photodiode (30) is assigned.

4. The device according to claim 1, wherein a polarization filter (32) is arranged between the source of light (14) and the at least one detector (20) whereby an absorption filter (34) is assigned to the detectors (20).

5. The device according to claim 1, wherein a wave length of the source of light (14) lies in the range of 600 nm up to about 1200 nm.

6. The device according to claim 5, wherein the wave length of the source of light is about 820 nm.

7. The device according to claim 1, wherein at least one of the plurality of superficial areas (22) and a corresponding detector (20) are arranged along a straight line (40) running through the first area (16) and symmetrically in pairs on both sides of the first area (16).

8. The device according to claim 1, wherein at least one of the plurality of superficial areas (22) and said at least one detector (20), respectively, are arranged at a maximum distance (56) of up to about 15 to 30 mm away from the first area (16).

9. The device according to claim 1, wherein two signals (42, 44) registered by the superficial areas (22) arranged in pairs are both transmitted to two inputs of a differential amplifier (46).

10. The device according to claim 1, wherein the source of light (14) as well as the detectors (20) and an electronic component, and a differential amplifier (46) are housed together in a measuring head (58) that is placeable flatly onto the tissue (12) whereby the measuring head (58) is connectable to an evaluation unit via an electric conductor.

11. The device according to claim 1, wherein said depth of said detected blood flow increases as said distance between said superficial area and said first area increases.

12. A device (10) for a non-invasive detection of one of a blood flow and intracorporeally and extracorporeally flowing liquids in one of a human and animal tissue (12); said device comprising a coherent, monochromatic source of light (14) including a laser, for emission of a plurality of photons into the tissue (12), through a first area (16) of skin (18) covering the tissue (12), at least one detector (20) for registering the photons reemerging from one of a plurality of superficial areas (22) of the skin (18) whereby the plurality of superficial areas (22) are located at different distances from the first area (16); and a detection means for selectively detecting a blood flow a selective depth below said skin, wherein said plurality of superficial areas (22) are serially arranged in pairs disposed on opposing sides of a line (100) extending from said first area and a corresponding pair of said plurality of detectors (20) are resperctivley arranged proximate said pairs of superficial areas and essentially in series, whereby each pair of superficial areas has a predetermined distance from the first area (16) and distances between neighboring pairs of superficial areas are equidistant.

13. A device (10) for a non-invasive detection of one of a blood flow and intracorporeally and extracorporeally flowing liquids in one of a human and animal tissue (12); said device comprising a coherent, monochromatic source of light (14) including a laser, for emission of a plurality of photons into the tissue (12), through a first area (16) of skin (18) covering the tissue (12), at least one detector (20) for registering the photons reemerging from one of a plurality of superficial areas (22) of the skin (18) whereby the plurality of superficial areas (22) are located at different distances from the first area (16); and a detection means for selectively detecting a blood flow a selective depth below said skin, wherein a plurality of signals of the detectors (20) are submitted to an adaptive filter function (52) as well as to a cepstrum analysis function (78).

14. An evaluation procedure for detecting one of a blood flow and an intracorporeally and an extracorporeally flowing liquid in one of a human, and animal biological tissue (12) at a selective depth below said tissue, comprising the steps of:

entering photons of a coherent, monochromatic source of light (14) into the biological tissue (12) of a first area (16), said photons reemerging at a plurality of superficial areas of different distances from said first area (16); wherein each of said superficial area corresponds to a specific depth of said one of said blood flow and flowing liquids;

determining said specific depth of each of said superficial areas by a known relationship with a distance between said superficial areas and said first area;

detecting said reemerging photons with respect to one of a frequency and a number and an intensity of said photons, and generating, by using an evaluation program conclusions about a relative modification of one of an amount of speed and a location of one of the blood flow and flowing liquids flowing in the tissue (12) at said specific depth from one of said frequency and number and intensity of said reemerging photons.

15. The evaluation procedure according to claim 14, wherein said step of entering photons comprises a source of light (14) with a high coherence length being higher than 10 cm.

16. The evaluation procedure according to claim 15, further comprising a step of generating a plurality of signals representative of said frequency and said number and said intensity of said reemerging photons, and the signals of two superficial areas (22) are transmitted to a differential amplifier function (46).

17. The evaluation procedure according to claim 15, further comprising a step of generating a plurality of signals representative of said frequency and said number and said intensity of the detected reemerging photons of two superficial areas (22) and submitting said signals to at least one of a frequency and a cepstrum analysis function (78).

18. The evaluation procedure according to claim 14, wherein the photons reemerging at a given distance from the first area (16) are simultaneously detected in two superficial areas (22) arranged adjacent to the first area (16).

19. An evaluation procedure for detecting one of a blood flow and an intracorporeally and an extracorporeally flowing liquid in one of a human, and animal biological tissue (12), comprising the steps of:

entering photons of a coherent, monochromatic source of light (14) into the biological tissue (12) of a first area (16), said photons reemerging at different distances from said first area (16) are detected with respect to one of a frequency and a number and an intensity of said photons, generating a plurality of signals representative of at least one of said frequency and said number and said intensity of said reemerging photons, and generating, by using an evaluation program conclusions about a relative modification of one of an amount of speed and a location of one of the blood flow and flowing liquids flowing in the tissue (12) from one of said frequency and number and intensity of said reemerging photons, wherein said step of entering photons comprises a source of light (14) with a high coherence length being higher than 10 cm, wherein the detected signals of two superficial areas (22) are submitted to an adaptive filter function (52) for determination of blood flow a selective depth below the skin.

20. A device (10) for a non-invasive detection of a blood flow in a human comprising:

a coherent, monochromatic source of light (14) including a laser for emission of a plurality of photons into the tissue (12), through a first area (16) of skin (18) covering the tissue (12), a plurality of opposing pairs of detectors serially positioned discretely along a line extending from said first area adjacent a corresponding superficial area of skin surface of said human; said detectors registering the photons reemerging from said skin at said superficial areas (22) of the skin (18); and a detection means for selectively detecting said blood flow a specific depth below said skin, wherein said specific depth corresponds to said distance of said superficial area to said first area.

* * * * *